United States Patent [19]

Waluda

[11] Patent Number: 5,761,975
[45] Date of Patent: Jun. 9, 1998

[54] METHOD AND APPARATUS FOR DISPOSING OF USED SYRINGE NEEDLES

[76] Inventor: Casey E. Waluda, 5431 NE. River Rd., Chicago, Ill. 60656

[21] Appl. No.: 524,300

[22] Filed: Sep. 6, 1995

[51] Int. Cl.$^6$ .................................................. B23B 5/14
[52] U.S. Cl. .......................... 82/58; 82/59; 83/54; 83/944
[58] Field of Search ...................... 83/944, 54, 471.1; 82/58, 59, 54

[56] References Cited

U.S. PATENT DOCUMENTS

| | | | |
|---|---|---|---|
| 1,306,588 | 6/1919 | France | 82/59 |
| 3,129,621 | 4/1964 | Makowski | 82/59 |
| 3,322,355 | 5/1967 | Bryant | 241/186 |
| 3,683,733 | 8/1972 | Johan et al. | 83/944 |
| 3,750,966 | 8/1973 | Anderson | 241/99 |
| 3,796,359 | 3/1974 | Dick | 225/93 |
| 4,111,346 | 9/1978 | Bertolette | 82/59 |
| 4,255,996 | 3/1981 | Choksi et al. | 83/140 |
| 4,315,448 | 2/1982 | Ball | 83/944 |
| 4,565,311 | 1/1986 | Pugliese et al. | 83/944 |
| 4,862,573 | 9/1989 | Kelson et al. | 29/240 |
| 4,905,552 | 3/1990 | Shinbori | 82/59 |
| 4,961,541 | 10/1990 | Hashimoto | 241/65 |
| 4,971,261 | 11/1990 | Solomons | 241/99 |
| 4,986,811 | 1/1991 | Thead et al. | 604/110 |
| 5,035,367 | 7/1991 | Nojima | 241/37.5 |
| 5,188,598 | 2/1993 | Thead et al. | 604/110 |

*Primary Examiner*—Kenneth E. Peterson
*Attorney, Agent, or Firm*—Arnold, White & Durkee

[57] ABSTRACT

Syringe needles are cut in an efficient manner and safely disposed using a cutting mechanism and a disposal container. The cutting mechanism includes two discs with sharp edges. The discs are displaced toward each other and into an overlapped position. At the same time, the circular discs are rotated around the longitudinal axis of the needle at a high angular velocity and are allowed to pivot upon coming in contact with the needle. The cutting and disposal apparatus includes a housing with a syringe receptacle for receiving the needle of a syringe and a used needle disposal container. The used needle disposal container has an orifice in alignment with the syringe needle receptacle in the housing. A switch associated with the syringe needle receptacle when the syringe needle syringe is inserted into the receptacle automatically activates a motor which imparts the displacement and rotational motion and causes the discs to pivot around their center upon contact with the needle to slice the needle off of the syringe. After the needle is cut off, it falls into the used needle disposal container placed directly below the syringe receptacle. The disposal container is permanently locked and sealed after it is removed from the cutting and disposal device. The container is made preferably from the same type of metal as the syringe needles so that the container together with the used syringe needles inside it can be melted to produce recycled metal.

9 Claims, 5 Drawing Sheets

METHOD AND APPARATUS FOR DISPOSING OF USED SYRINGE NEEDLES

BACKGROUND OF THE INVENTION

The present invention is directed to disposal devices for disposing of used syringe needles. In particular, the present invention is directed to a method and an apparatus for disposing of used syringes by cutting off used syringe needles and then storing the cut-off needles in a secured container.

Each year thousands of syringe hypodermic needles are used by hospitals, clinics and other medical facilities. To avoid contamination, practically all needles and most syringes are used only once. After the needles or syringes are used, they have to be properly disposed. One approach for suitable disposal of syringes is to place the syringes with the needles still attached to them into sealed containers. The containers are then periodically emptied into disposal machines. The disposal machines pulverize, sterilize or incinerate the content of the containers so that the resulting ground and sterilized or incinerated particles could be safely placed in a landfill or other non-hazardous disposal sites. For example, U.S. Pat. No. 4,971,261 to Solomans discloses a device for fragmenting medical waste, including syringes. The device disclosed in the Solomans patent includes a U-shaped stationary member to hold the item to be fragmented and a rotating blade which fragments the item in a shearing-type action. The device also includes an agitating member which continually throws the cut fragments into the path of the rotating blade to further cut the fragments into particles that are sufficiently small to be disposed of after sterilization. Similarly, U.S. Pat. No. 4,565,311 to Pugliese et al. discloses a machine for destroying used syringes. The machine includes a pair of spaced apart knives which shear parts of the syringe in multiple locations. U.S. Pat. No. 4,961,541 to Hashinoto et al. discloses a hypodermic syringe disposal apparatus which employs mesh gears to crush the syringe. Electrical voltage is applied to the gears so that the hypodermic needle of the syringe is burnt immediately upon coming in contact with the gears. U.S. Pat. No. 3,750,966 to Anderson discloses a device for destroying syringes, which employs a pair of counter-rotating toothed rolls for fracturing syringes into discrete pieces. U.S. Pat. No. 3,322,355 to Bryant discloses a disintegrating machine which grinds hypodermic syringes into small pieces. Finally, U.S. Pat. No. 5,035,367 discloses a device which crushes medical waste using rotating blades that shear the items into pieces.

The approach of disposing of syringe needles by grinding crushing or pulverizing the entire syringe presents several problems. First, the devices for crushing the entire syringe, including the hypodermic needle, are generally, large, heavy and not easily portable. Therefore, the syringes have to be transported to such devices and, in most cases, the syringes must be temporarily stored prior to being transported. The sharp hypodermic needles on the syringes present a risk that either the medical personnel or the disposal personnel become infected by pricking their skin on the needles during storage or transportation. Second, the syringes can be stolen from temporary storage places or during transport and then reused by drug addicts. Third, the machines for crushing or grinding entire syringes are generally noisy and they vibrate during operation. This necessitates special arrangements for accommodating such machines. Finally, since tremendous forces have to be generated to crush syringes, the crushing machines are relatively expensive to make. They are also expensive to maintain because the parts subjected to stresses wear out requiring frequent maintenance to replace or repair worn out parts.

To obviate the problems inherent in the disposal of used hypodermic needles by crushing or grinding entire syringes, various devices have been designed for the removal of used syringe needles from the syringes, and subsequent disposal of the removed needles separately from the syringes. An inherent problem with removing the used needles from the syringes is the risk of accidental pricking of the skin which may cause infection from a virus, bacteria or microorganism that may be present on the needle.

To address this risk, devices were introduced to automatically unthread or unscrew the hypodermic needles from the syringes and to store the separated needles. For example, U.S. Pat. No. 4,862,573 to Kelson, et al. discloses a disposal device for blood sampling needles in which a needle is threaded into a reusable sleeve. After the sampling needle is used to draw blood, the needle is unthreaded from the sleeve and discarded. The sleeve may be reused then with a new needle. The disposal device disclosed in the Kelson et al. patent automatically unscrews the needle from the sleeve when the blood sampling needle is inserted into the disposal device. U.S. Pat. No. 4,986,811 to Thead, et al. also discloses an apparatus for removing disposable needles from reusable syringes by unscrewing them from the body of the syringe. The user inserts the needle into the apparatus which automatically rotates the needle to disconnect it from the syringe. Similarly, the Thead et al. '598 patent, discloses a device which unscrews the needle from the syringe and allows the used needle to fall into a container. The device of this patent removes but does not destroy the used hypodermic needles.

One disadvantage of the devices that merely unscrew or unthread used needles from syringes is that the needles are not destroyed immediately after being separated from the syringes. As a result, the used needles that are temporarily stored, transported or discarded can be recovered by drug users, for example, and reused. The recovered needles that are not properly sterilized before being used again may contribute to the spread of infectious diseases.

One approach to disposal of syringe needles is to snap, shear or bend the syringe needle so that it cannot be reused. This approach is disclosed in several patents. For example, U.S. Pat. No. 4,255,996 to Choksi et al discloses a device for severing a hypodermic needle at cannula using a manual cutter. The Choksi et al patent discloses that the cutter should preferably have a blunt shearing edge. It notes that a very sharp, beveled edge would simply dull when abutting the metal cannula. See e.g. column 2, lines 37–41. U.S. Pat. No. 3,796,359 to Dick discloses a syringe needle destroyer having a conical needle guide provided in axial alignment with a relatively small cylindrical passageway. To dispose of a used needle, the needle is inserted into the passageway via the needle guide and the syringe is bent to snap the needle off of the syringe by the bending action. The needle falls into a container for retaining used needles. One disadvantage of the device disclosed in the Dick patent is that the needle guide into which the needle must be inserted is so small that medical users of the device may inadvertently prick themselves with the used needles while attempting to insert the needle, and thus subject themselves to the risk of being infected with disease that may be carried on the contaminated needle. Another disadvantage of this approach is that the device for shearing or bending or snapping of syringe needles produce noise and vibration, both of which are disruptive in the hospital environment. Moreover, the large forces required to effect shearing bending or snapping of needles tend to reduce the useful life of such machines or require frequent maintenance to replace worn out parts.

There is, therefore, a long felt and still unsatisfied need for an efficient and safe manner of disposing of used syringe needles to prevent medical personnel and others from being infected by the used needles which may be contaminated with infectious agents and for an efficient and safe disposal of used syringe needles so as to prevent the contaminated needles from being reused and thereby minimize the spread of diseases.

The present invention fulfills these long felt still unsatisfied needs.

Thus, one object of the present invention is to provide an efficient and inexpensive method for disposing of syringes and hypodermic needles which renders the needles unusable and can be performed without excessive noise and vibration.

Another object of the present invention is to provide an efficient apparatus for disposing of syringes and hypodermic needles which is small enough to be portable and which requires a minimal amount of maintenance.

A further object of the present invention is to provide a method and an apparatus for disposing hypodermic needles which allows for secured storage and safe disposal of the needles cut off from the syringes.

Still another object of the present invention is to provide a method and an apparatus for disposing of syringe needles, that need not be serviced or maintained for a prolonged time.

A yet further object of the present invention is to provide a method and an apparatus for disposing of syringe hypodermic needles which does not require special accommodations to avoid noise and vibrations.

Other objects of the present invention will become apparent to those skilled in the art upon studying this disclosure. All such objects and all advantages and features of the present invention are intended to be included within the scope of the claimed invention.

SUMMARY OF THE INVENTION

The present invention provides an efficient, quiet and substantially maintenance-free method and apparatus for cutting off hypodermic syringe needles and securely storing the cut off needles in a disposal container. The needles are sliced off by displacing two sharp-edged discs toward each other and into an overlapped position on either side and adjacent to a plane that crosses the longitudinal axis of the needle while at the same time rotating the discs around the longitudinal axis of the needle and while allowing the discs to pivot around their centers once they come in contact with the needle.

In accordance with another feature of the present invention the circular discs are made of hardened steel or carbide and they are capable of cutting thousands of syringe needles before they need to be sharpened or replaced.

In accordance with yet another feature of the present invention, a secured disposal container is used receiving and storing the cut-off syringe needles. The container is locked and sealed when it is removed from the needle disposal device. The disposal device includes a housing with a receptacle for receiving a needle of a syringe. The used needle container has an orifice in alignment with the syringe receptacle in the housing. The needle disposal device includes a switch associated with the syringe receptacle for automatically activating the cutting means to slice off the needle, once the syringe is inserted into the syringe needle receptacle. After the needle is sliced off, it falls into the used needle container placed directly below the syringe needle receptacle.

In accordance with a further feature of the present invention, the disposal device includes means for maintaining alignment of the used needle container with the syringe receptacle, such as a ridge formed in the bottom of the housing which surrounds and locates the bottom portion of the used needle container. The needle disposal device preferably also includes an indicator which specifies the number of needles which have been cut off and stored in the container.

These features and advantages of the present invention and additional features and advantages that will be apparent to those of ordinary skill in the art in view of this disclosure, are intended to be included within the scope of the claimed invention.

DETAILED DESCRIPTION OF THE INVENTION

Figure 1:
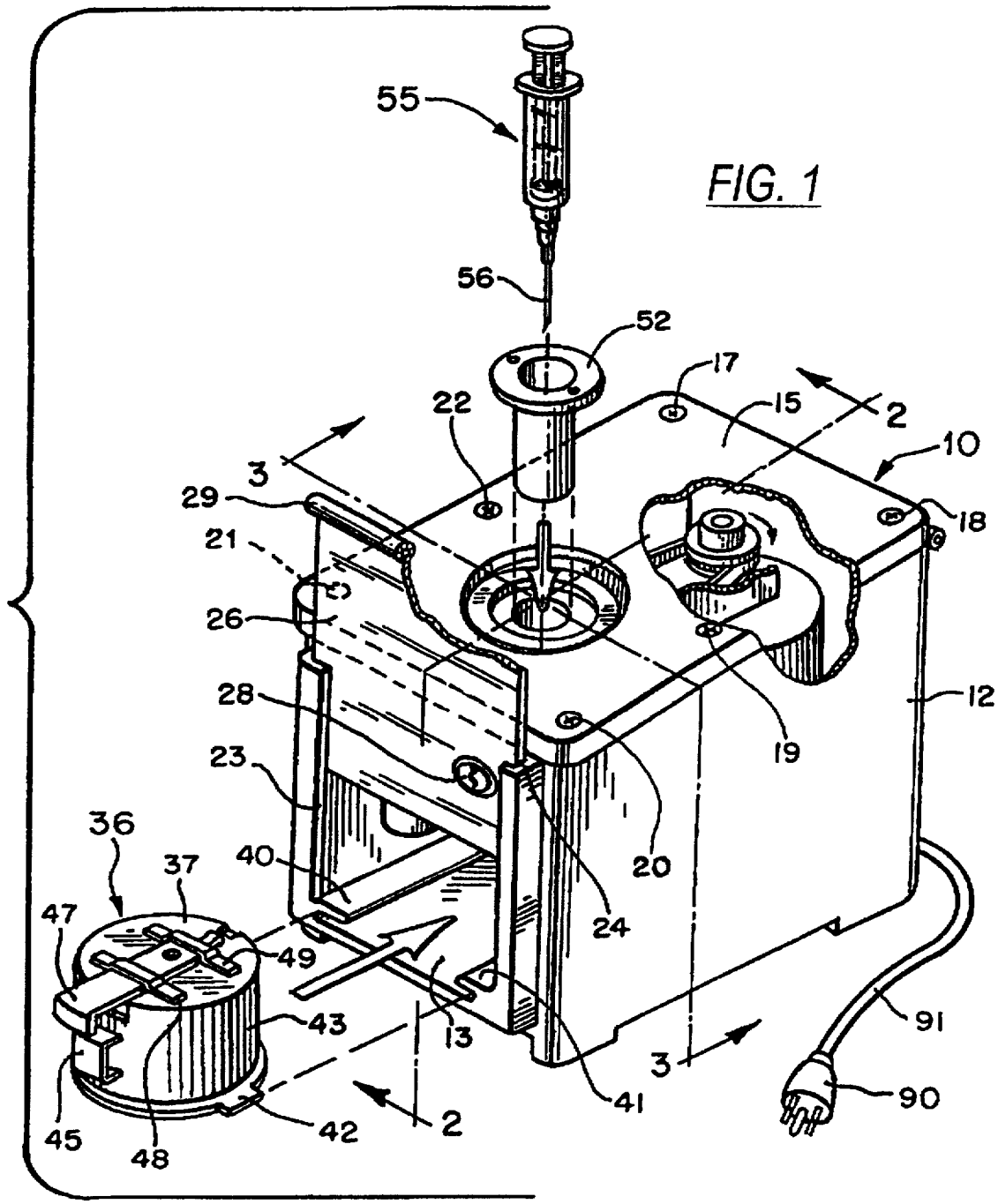
FIG. 1 is an exploded perspective view, with a cut-out section, of the preferred embodiment of a syringe needle cutting and disposal device constructed in accordance with the present invention.

It has been discovered that used syringe needles can be cleanly, efficiently and quietly sliced off from the syringes using sharp-edged discs which simultaneously move, rotate and pivot to slice through the needles. The sliced off needles are directed into a container by a guide. Once the container is full, it is locked and sealed. The container is preferably made of the same metal (generally a high grade steel) as the syringe needles so that the filled container can be melted to produce recycled metal.

The present invention employs discs with sharp cutting edges. Generally, the radius of the cutting edges is in the range from about 0.002" to about 0.015", preferably in the range from about 0.002" to about 0.005." The sharp edges of the discs are initially located on opposite sides of longitudinal axis of a syringe needle which is maintained in a fixed position. The discs are displaced on either side and adjacent to a plane, that crosses the longitudinal axis of the syringe needle, toward each other and into an overlapped position. At the same time, the discs are rotated around the longitudinal axis of the needle and upon coming in contact with the syringe needle they are allowed to pivot around their centers. As the result of these three motions the discs cleanly slice across the longitudinal axis of the needle. The sharp edges of the discs overlap at the completion of the cut to assure a clean cut through the syringe needle.

Preferably, the cutting surfaces are the edges of circular discs and the slicing movement is achieved by displacing these discs while they are rotated at high speed around the longitudinal axis of the needle and pivoted around their centers. The discs are generally rotated around the longitudinal axis of the needle at speed in the range from about 5 RPM to about 5000 RPM, preferably, in the range from about 500 and about 3000 RPM. In the preferred embodiment the discs are rotated at about 2000 RPM. The speed of rotation must be sufficiently high to cause the centrifugal force to displace the discs from the rest position to the overlapped position. In the mechanism shown in the drawings, the discs must be rotated at a sufficiently high speed to generate a centrifugal force that is sufficient to pivot the brackets holding the circular discs to cause the discs to move into the overlapped position.

The cutting edges can be made from the same or different materials than the remainder of the discs. Preferably, the entire discs are made of the same material. The discs and/or the sharp cutting edges can be made of any suitable cutting material. However, the edges and the discs are preferably made of steel, and in particular, hardened steel. For applications where making maximum number of cuts is important, the discs can be made of carbide. In the alternative, the discs may have carbide cutting edges. It is believed that the hardened steel discs in the system of the present invention can generally cut about 100,000 needles before they need to be replaced or sharpened. It is also believed that generally, circular carbide discs employed in the system of the present invention can cut at least about a million needles before they need to be sharpened or replaced.

The size of the cutting discs depends on the particular operation. Generally, the discs have diameters in the range from about ⅛" to about 1", preferably in the range from about ¼" to about ⅝".

Figure 5:
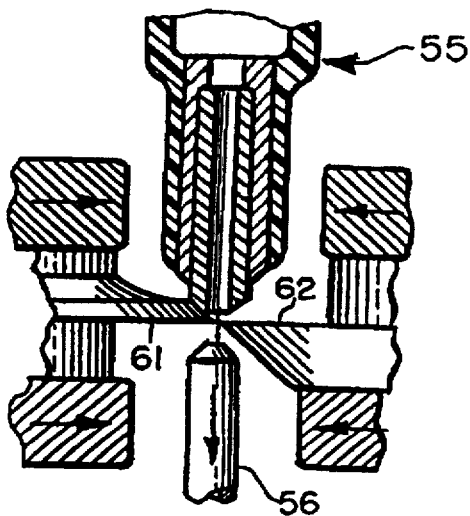
FIG. 5 is a partial cross-sectional view of the syringe aid of the cutting mechanism of the device of FIG. 1 shown shortly after the needle is cut off.
Figure 6:
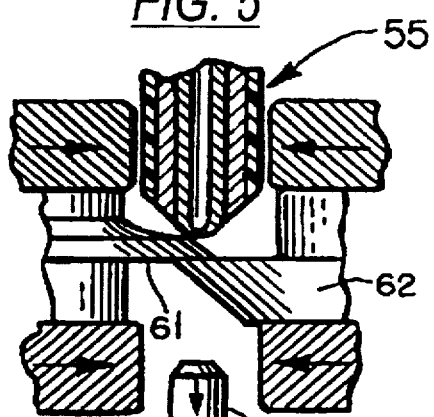
FIG. 6 is a cross-sectional view of the cutting mechanism of the device of FIG. 1, shown after the needle is cut off.

The present invention allows cutting of the needle at any location along the needle. However, the needle is preferably cut immediately adjacent the cannula of the plastic hub as shown in FIGS. 5 and 6. Moreover, the needle can be cut at a plane forming any angle with the longitudinal axis of the needle. However, it is preferred to cut the needle along a plane which is substantially perpendicular to the longitudinal axis of the needle. The reason this location and this configuration of the cuts are preferred is that when the needle is cut off at the cannula flush with the plastic, the danger stemming from punctures by the uncut portion of the needle remaining on the syringe is eliminated.

DETAILED DESCRIPTION OF THE PREFERRED EMBODIMENT

The present invention will now be further described in connection with the preferred embodiment shown in the drawings. The following description is intended to further illustrate the invention and it is not intended to limit the claimed invention in any manner.

Referring now to the drawings, FIG. 1 depicts a device 10 for cutting syringe needles and for disposing of the cut needles, constructed in accordance with the present invention. The device 10 includes generally vertical housing walls 12, a generally horizontal housing floor 13, and a cover 15. The cover 15 is attached to the walls 12 by six removable screws 17, 18, 19, 20, 21 and 22. The vertical walls 12 include two generally vertical U-shaped channels, 23 and 24 which accommodate a slidable door 26. The door 26 is equipped with a lock 28 and a handle bar 29.

Figure 2:
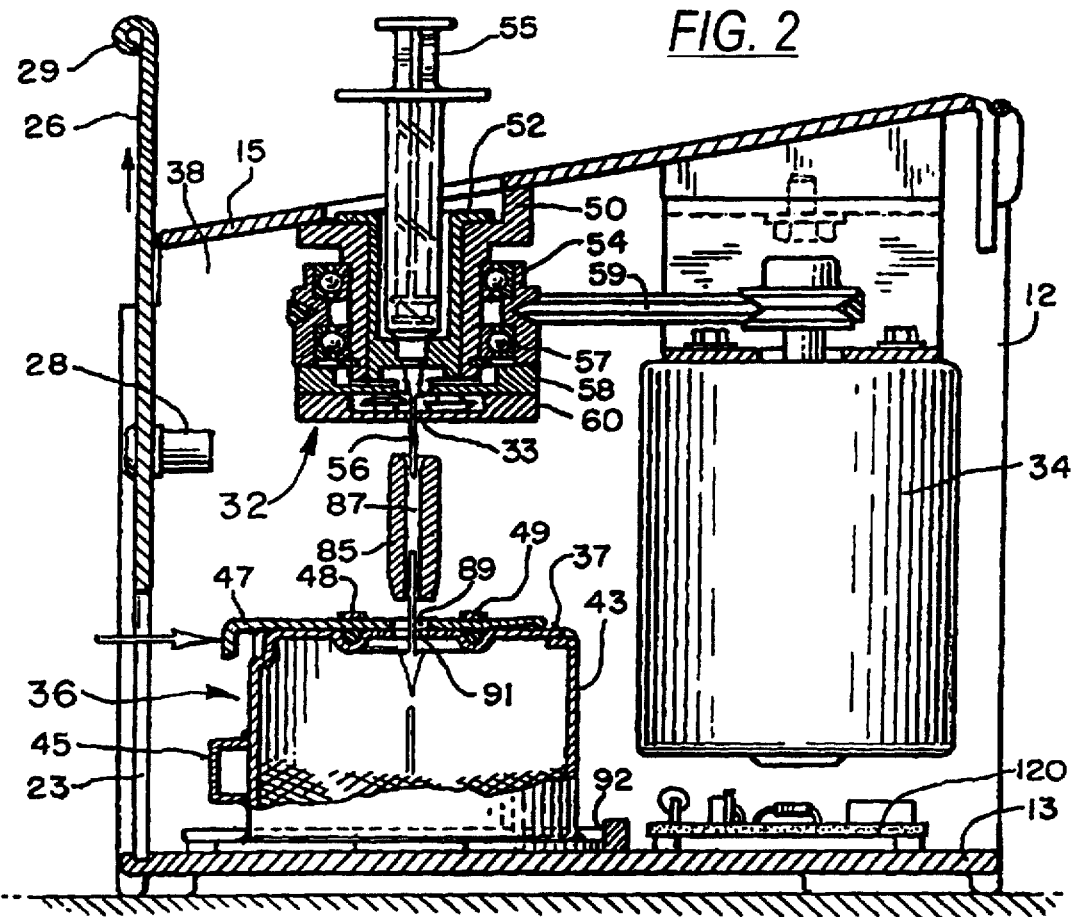
FIG. 2 is a cross-sectional view of the device of FIG. 1 taken along the line 2—2 thereof.
Figure 3:
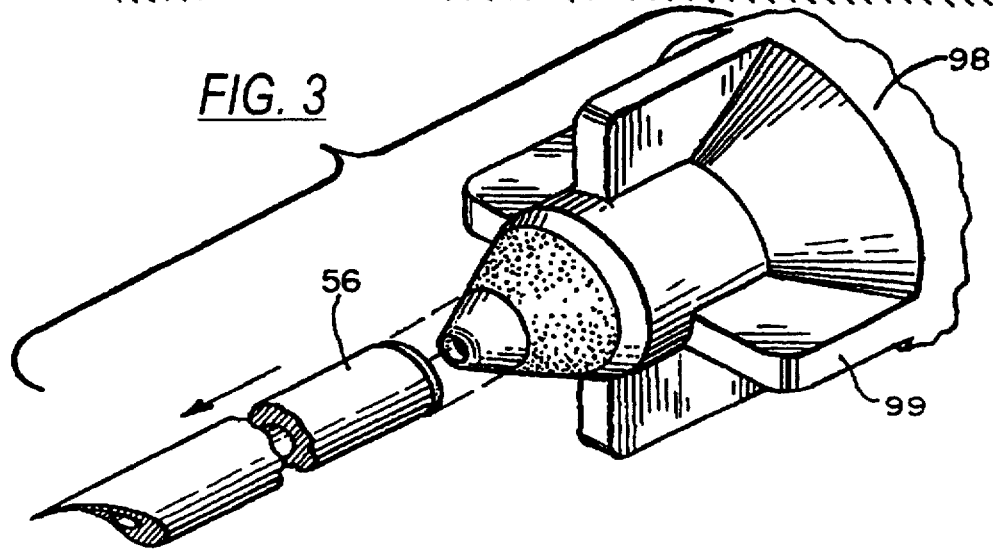
FIG. 3 is a perspective view of a portion of a syringe needle, a cannula and a needle hub.

As shown in FIG. 2, the housing walls 12, the floor 13, the cover 15 and the door 26 form a housing chamber 38 which accommodates a cutting assembly 32 of the device 10, an electrical motor 34 for powering the cutting assembly 32 and a disposal container 36. The disposal container 36 includes a circular top 37.

As shown in FIG. 1, the disposal container 36 includes two parallel legs 42 located on opposite sides of the generally cylindrical walls 43 of the container 36. When the container 36 is slid into the housing chamber 38, the legs 42 slide in the grooves formed between ledges 40 and 41 and the floor 13. To facilitate sliding of the container 36 into and out of the housing chamber 38, the container 36 is provided with a handle 45. The container 36 also includes a slide 47 which is slidably mounted to the top 37 of the container 36 by two parallel brackets 48 and 49.

As shown in FIG. 2, the cutting assembly 32, includes a stationary fixed support member 50 which is rigidly affixed to the cover 15. A removable sleeve holder 52 is positioned inside the fixed support member 50. The sleeve holder 52 is designed to accommodate and hold in a fixed position a syringe 55. The sleeve holder 52 is removable so that it can be easily cleaned and so that it can be replaced with a holder designed to accommodate a syringe of a different shape.

Figure 4:
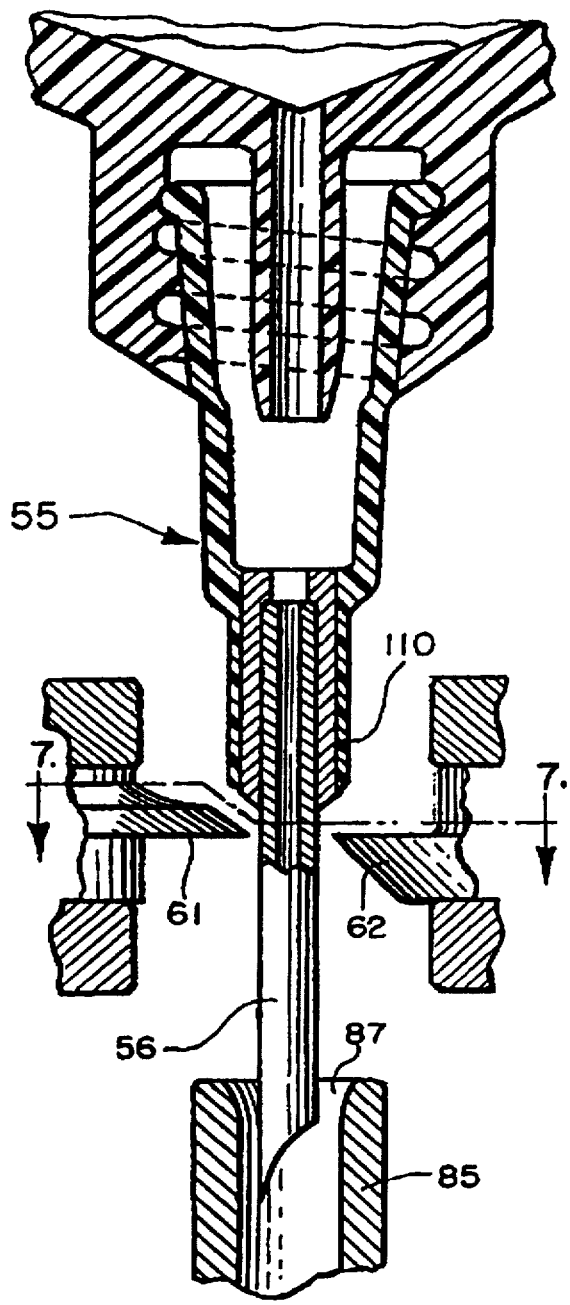
FIG. 4 is an enlarged partial cross-sectional view of portions of the syringe and of the cutting mechanism of the device of FIG. 1.
Figure 8:
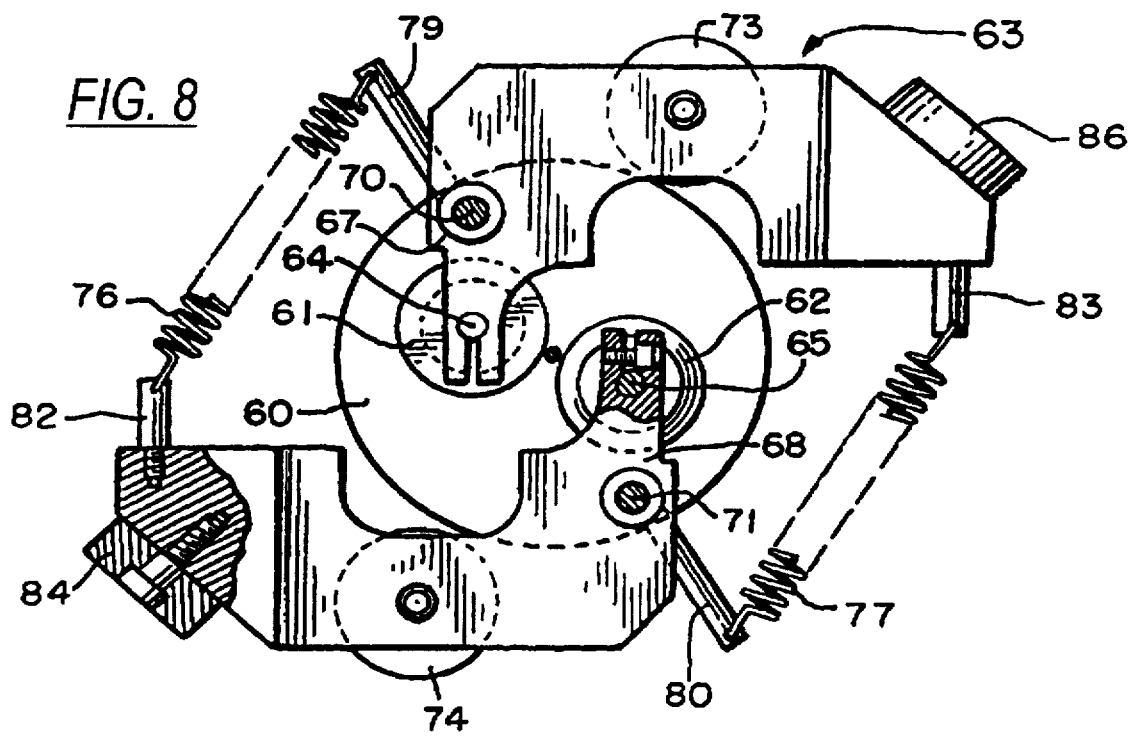
FIG. 8 is a plan view of the needle cutting mechanism of the device of FIG. 1.

As further shown in FIG. 2 an annular member 54 is rotatably connected to the outside surface of the fixed support 50 on bearings 57. The annular member 54 is rotated together with the members 58 and 60 by a belt 59 that is powered by the electrical motor 34. The rotation of the annular member 54 and members 58 and 60, causes rotation of a cutting mechanism 63, which is shown in detail in FIG. 8. Referring now to FIG. 8, the cutting mechanism 63, includes rotatably mounted circular cutting discs 61 and 62. The discs in the preferred embodiment shown in the figures are ½" in diameter and are made of D2 hardened steel. As shown in FIGS. 4–6, the discs 61 and 62 have sharp edges. The radii of the discs shown in the preferred embodiment are about 0.003".

As shown in FIG. 8, the discs 61 and 62 pivot (or rotate) around pivot needle bearings 64 and 65 at their centers. The discs 61 and 62 are removably mounted in the brackets 67 and 68, respectively. The brackets 67 and 68 are, in turn, mounted on pivot rods 70 and 71, respectively. Weights 73 and 74 are attached to the brackets 67 and 68, respectively. In the preferred embodiment, the weights 73 and 74 are steel cylinders attached to the brackets 67 and 68 by screws. The steel cylinders in the preferred embodiment are ¾ inch in diameter and ⅝ inch in height. The weights can be adjusted depending on the particular operation. Two springs 76 and 77 are provided to keep the discs 61 and 62 away from the needle 56 in the rest position. Each of the springs 76 and 77 is attached at one end to a rod 79 and 80, respectively. The rods 79 and 80 are attached to the member 60. At the other end, each of the springs 76 and 77 is attached to an insert pin 82 and 83, respectively. The insert pins 82 and 83 are threaded into the brackets 67 and 68, respectively. In the rest position, the springs 76 and 77 maintain the brackets 67 and 68, respectively, in a position where the discs 61 and 62 are located on either side of and away from the needle 56 of the syringe 55. A washer 84 is attached to the bracket 68 and a washer 86 is attached to the bracket 67.

As shown in FIG. 2, when the syringe 55 is in the holder 52, the needle 56 extends down past a circular opening 33 in the member 60 and into a bore 87 in a guide tube 85. The guide tube 85 is held in position by brackets (not shown) attached to the walls 12. As also shown in FIG. 2 and in FIG. 4, the bore 87 has a diameter larger than the outside diameter of the needle 56 so that the needle 56 can freely fall through the guide tube 85 after cutting. The bore 87 is aligned with the longitudinal axis of the needle 56, with the opening 89 in the slide 47 and the opening 91 in the container 36, when the slide 47 is in the open position, as shown in FIGS. 1 and 2.

In operation, the container 36 with the slide 47 in the open position (so that openings 89 and 91 are aligned with each other), is slid into the chamber 38, as indicated by an arrow in FIG. 1. The legs 42 travel along and inside the channels formed between the bottom 13 and the ledges 40 and 41 until the container 36 reaches a stop position defined by a ledge 92, shown in FIG. 2. In the stop position, the openings 89 and 91 are aligned with the bore 87 of the guide tube 85. The door 26 is then slid down along the vertical channels 23 and 24 to a closed position and the lock 28 is engaged to prevent unauthorized entries to the container 36. An electrical plug 90, attached to an electrical cord 91 connected to the motor 34, is plugged into an electrical socket (not shown). The syringe 55 is then inserted into the sleeve holder 52 so that it is rigidly held in position for cutting. The sleeve 52 is prevented from rotating by pins (not shown) which connect it to the member 50. Two projections extending from the sleeve holder 52 (not shown) fit between wings 99 on opposite sides of the cylindrical part 98 of the hub 110 and prevent the rotation of the syringe 55.

Figure 7:
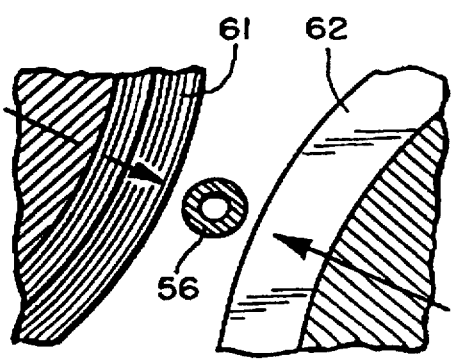
FIG. 7 is a cross-sectional view of the cutting discs approaching the needle in the device of FIG. 1.
Figure 10:
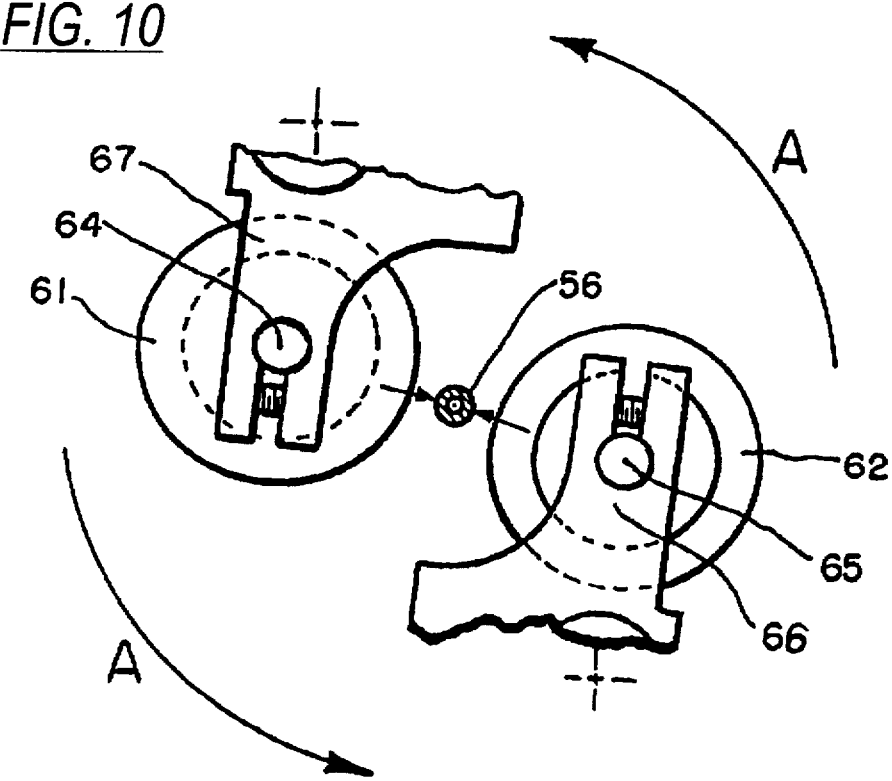
FIG. 10 is a partial plan view of the cutting mechanism of FIG. 8 showing the directions of the displacement and rotation of the discs in the cutting mechanism.
Figure 11:
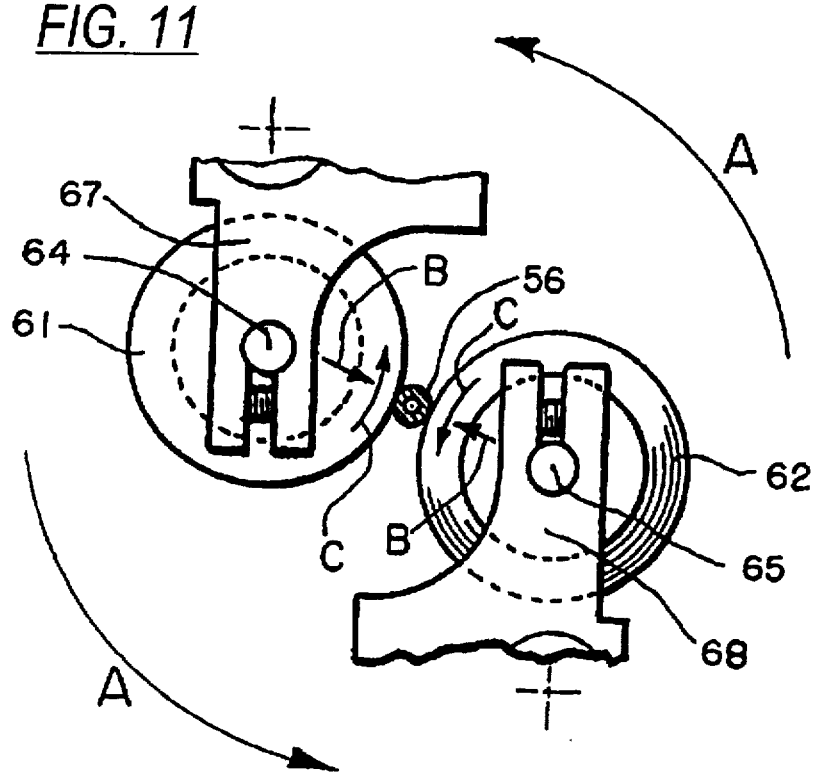
FIG. 11 is a partial plan view of the cutting mechanism of FIG. 8 showing the direction of the displacement, rotation and pivoting of the discs upon contact with the needle in the cutting mechanism.

As shown in FIG. 2, FIG. 4 and in FIG. 7, in the rest position, the cutting discs 61 and 62 are on opposite sides of the longitudinal axis of and away from the needle 56. Once the syringe needle 56 is in the position shown in FIG. 2, the motor 34 is activated by a micro-switch between the sleeve holder 52 and the member 50 (not shown). The motor 34 drives the belt 59, which, in turn, rotates the members 57, 58 and 60 at a preferred speed of about 2000 RPM around the longitudinal axis of the needle 56 in the direction designated by "A" in FIGS. 10 and 11. The centrifugal force generated by this rotation, causes the weights 73 and 74 (shown in FIG. 8) to move outwardly away from the needle 56. The outward movement of the weights 73 and 74, in turn, causes the brackets 67 and 68 to pivot around their respective pivot rods 70 and 71, against the forces of their respective springs 76 and 77. The pivoting of the brackets 67 and 68 moves the edges of the discs 61 and 62 toward the needle 56, in the direction shown by arrows in FIGS. 7 and 10 and designated by arrows "B" in FIG. 11. The sharp edges of the discs 61 and 62 are displaced from the position shown in FIG. 4 toward each other and toward the needle 56 of the syringe 55. Upon coming in contact with the needle 56 the discs 61 and 62 are caused to pivot (or rotate) around their respective needle bearings 64 and 65 in the direction by arrows "C" in FIG. 11. Allowing the discs 61 and 62 to pivot extends the life of the sharp edges and facilitates slicing of the needle. If the discs 61 and 62 were fixed with respect to the respective brackets 67 and 68, the edges would become dull and worn out much quicker and the needle would not be cut as efficiently. As the edges of the rotating discs 61 and 62 come in contact with the needle 56, they slice through it immediately below the cannula of the needle hub 110, as shown in FIG. 5. To assure a clean cut, the edges of the discs 61 and 62 are moved past longitudinal axis of the needle 56 into an overlapped position, as shown in FIG. 6.

As shown in FIG. 2, the cut-off portion of the needle 56 falls through the bore 87, through the openings 89 and 91 into the container 36. An electronic eye controller (not shown) detects the needle 56 falling through the bore 87 of the guide 85 and sends a signal to a master controller 120 which sends a signal to turn off the motor 34. In the alternative, the motor can be stopped when the washers 84 and 86 interrupt a light beam in the chamber 38. This approach is not shown in the drawings and is not currently preferred.

Figure 9:
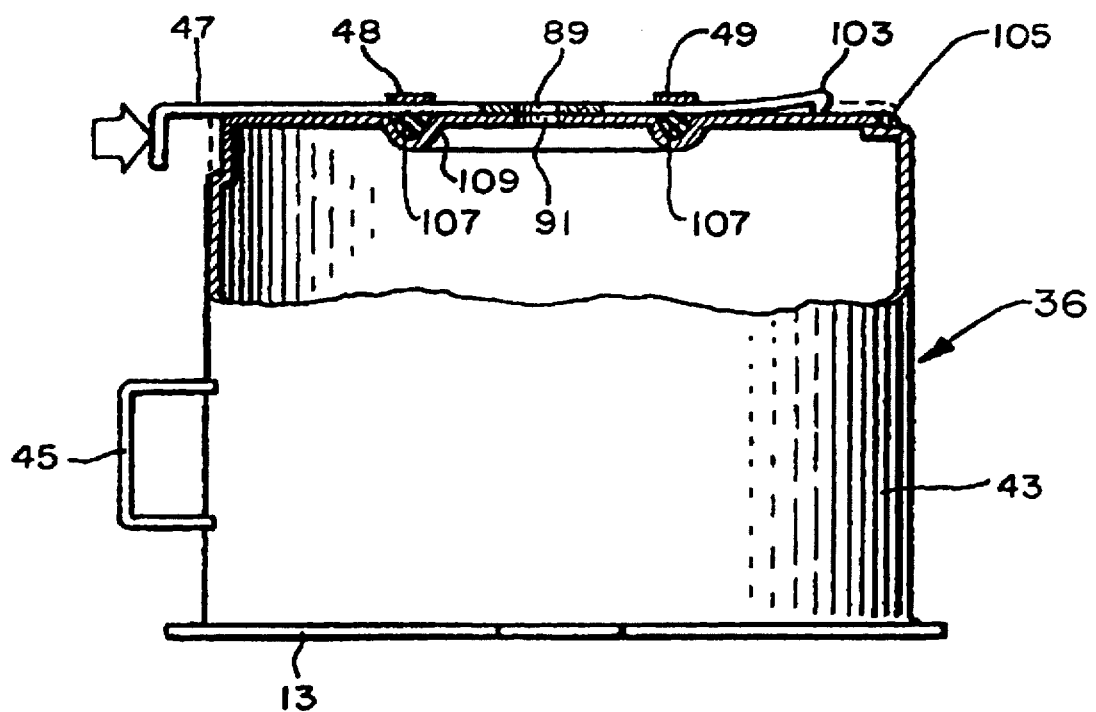
FIG. 9 is a side elevational view, partly in cross-section, of the disposal container of the device of FIG. 1.

The assembly 32 preferably includes an electronic counter (not shown) to keep track of the number of needles that are put in the container 36. Once the container 36 reaches its capacity, the lock 28 on the door 26 is unlocked. The door 26 is then slid open. The slide 47 of the container 36 is pushed toward the center so that, as shown in FIG. 9, the finger 103 becomes engaged in the notch 105 once the slide 47 reaches its fully closed position (shown in phantom lines in FIG. 9). In this position, the container 36 is securely closed. As can be seen in FIG. 9, in the fully closed position, the rubber O-ring 107 in the recess 109 of the top 37 seals the opening 91 so that any blood or other liquid transferred into the disposal container 36 with the cut-off needles is prevented from leaking out of the disposal container 36. The disposal container 36 cannot be easily opened because the finger 103 is wedged and resiliently engaged in the notch 105 in the top surface 37.

Once the disposal container 36 is sealed and secured by closing the slide 47, it is removed from the chamber 38, using the handle 45, and sent for proper disposal. Preferably, the container 36 together with the cutoff needles is melted to produce scrap metal.

Further modifications and alternative embodiments of the invention will be apparent to those skilled in the at in view of the foregoing description. The description of the preferred embodiment is to be construed as illustrative only, and is for the purpose of teaching those skilled in the art the best mode of carrying out the invention. The details of the structure and method may be varied substantially without departing from th spirit of the invention, and the exclusive use of all modifications which come within the scope of the appended claims is reserved.

What is claimed is:

1. An improved method for disposing of a used syringe needle, said method comprising the following steps:

(a) maintaining the syringe needle in a fixed position;

(b) displacing a first disc and a second disc toward each other until said first disc overlaps said second disc along opposite sides of and adjacent to a displacement plane which crosses the longitudinal axis of the needle, said first disc and said second disc having sharp edges and being initially located on opposite sides of the longitudinal axis of the needle;

(c) rotating said first disc and said second disc around longitudinal axis of the needle at a sufficiently high rate so that centrifugal force causes the displacing of step (b); and, (d) allowing said first disc and said second disc to pivot about their respective center pivot points upon coming in contact and as a result of the contact with the needle while said discs are being displaced and rotated around said longitudinal axis of the needle, so that said sharp edges slice through the needle and cut it off.

2. The method of claim 1 wherein the sharp edges are displaced along the displacement plane, which is substantially perpendicular to said longitudinal axis of the needle.

3. The method of claim 1 wherein said first disc and said second disc are rotated adjacent to the displacement plane.

4. The method of claim 3 wherein the discs are rotated in step (c) at between about 5 RPM and about 5000 RPM.

5. The method of claim 3 wherein the discs are rotated in step (c) at between about 500 and about 3000 RPM.

6. The method of claim 3 wherein the discs are rotated in step (c) at about 2000 RPM.

7. The method of claim 3 wherein the sharp edges slice the needle with the radius in the range from about 0.002" to about 0.015".

8. The method of claim 3 wherein the sharp edges slice the needle with the radius in the range from about 0.002" to about 0.005".

9. The method of claim 1 wherein the needle is attached to a cannula and the sharp edges slice the needle immediately adjacent to the cannula.

* * * * *